United States Patent
Iorgulescu et al.

(10) Patent No.: US 12,150,731 B2
(45) Date of Patent: Nov. 26, 2024

(54) SYSTEMS AND METHODS FOR SELECTIVELY ACTIVATING VIRTUAL GUIDE GEOMETRIES

(71) Applicant: MAKO Surgical Corp., Weston, FL (US)

(72) Inventors: Radu Iorgulescu, Boca Raton, FL (US); Carinne Cecile Granchi, Weston, FL (US); Dennis Moses, Hollywood, FL (US); Jason Robert Wojcik, Weston, FL (US)

(73) Assignee: MAKO Surgical Corp., Weston, FL (US)

( * ) Notice: Subject to any disclaimer, the term of this patent is extended or adjusted under 35 U.S.C. 154(b) by 0 days.

(21) Appl. No.: 18/396,892

(22) Filed: Dec. 27, 2023

(65) Prior Publication Data

US 2024/0122666 A1    Apr. 18, 2024

Related U.S. Application Data

(63) Continuation of application No. 18/198,424, filed on May 17, 2023, now Pat. No. 11,890,074, which is a
(Continued)

(51) Int. Cl.
*A61B 34/20* (2016.01)
*A61B 34/00* (2016.01)
(Continued)

(52) U.S. Cl.
CPC .............. *A61B 34/76* (2016.02); *A61B 34/20* (2016.02); *A61B 34/25* (2016.02); *A61B 34/30* (2016.02); *G06F 3/016* (2013.01); *G06F 3/0346* (2013.01); *G06F 3/0482* (2013.01); *G06F 3/04847* (2013.01); *A61B 2034/2055* (2016.02);
(Continued)

(58) Field of Classification Search
CPC ......... A61B 34/76; A61B 34/25; A61B 34/30; A61B 34/20; G06F 3/016; G06F 3/0346; G06F 3/0482; G06F 3/04847
See application file for complete search history.

(56) References Cited

U.S. PATENT DOCUMENTS 5,564,437 A  10/1996  Bainville et al.
7,319,892 B2  1/2008  Kato
(Continued)

FOREIGN PATENT DOCUMENTS

WO   WO-2011/109041 A1   9/2011

*Primary Examiner* — Benyam Haile
(74) *Attorney, Agent, or Firm* — FOLEY & LARDNER LLP

(57) ABSTRACT

A method for operating a surgical robot includes providing a plurality of virtual haptic geometries associated with different steps of a surgical procedure, evaluating a plurality of criteria associated with a first virtual haptic geometry of the plurality of virtual haptic geometries, activating the first virtual haptic geometry of the plurality of virtual haptic geometries without activating a second virtual haptic geometry of the plurality of virtual haptic geometries in response to satisfaction of the plurality of criteria, and controlling the surgical robot to constrain movement of an end effector of the surgical robot to the first virtual haptic geometry in response to activating the first virtual haptic geometry.

19 Claims, 8 Drawing Sheets

Related U.S. Application Data continuation of application No. 17/591,254, filed on Feb. 2, 2022, now Pat. No. 11,723,740, which is a continuation of application No. 16/777,301, filed on Jan. 30, 2020, now Pat. No. 11,259,888, which is a continuation of application No. 16/017,675, filed on Jun. 25, 2018, now Pat. No. 10,575,913, which is a continuation of application No. 15/583,739, filed on May 1, 2017, now Pat. No. 10,010,377, which is a continuation of application No. 13/340,668, filed on Dec. 29, 2011, now Pat. No. 9,639,156.

(51) Int. Cl.
*A61B 34/30* (2016.01)
*G06F 3/01* (2006.01)
*G06F 3/0346* (2013.01)
*G06F 3/0482* (2013.01)
*G06F 3/04847* (2022.01)
*G06F 3/033* (2013.01)
*G06F 3/0338* (2013.01)

(52) U.S. Cl.
CPC ............ *A61B 2034/2057* (2016.02); *A61B 2034/2068* (2016.02); *G06F 3/033* (2013.01); *G06F 3/0338* (2013.01)

(56) References Cited

U.S. PATENT DOCUMENTS

| | | | |
|---|---|---|---|
| 8,010,180 B2 | 8/2011 | Quaid et al. | |
| 8,287,522 B2 | 10/2012 | Moses et al. | |
| 8,391,954 B2 | 3/2013 | Quaid, III | |
| 8,882,662 B2 | 11/2014 | Charles | |
| 8,911,453 B2 | 12/2014 | Tenney et al. | |
| 2004/0024311 A1 | 2/2004 | Quaid, III | |
| 2004/0034283 A1* | 2/2004 | Quaid, III | A61B 34/76 600/300 |
| 2004/0106916 A1 | 6/2004 | Quaid et al. | |
| 2004/0128026 A1 | 7/2004 | Harris et al. | |
| 2006/0142657 A1* | 6/2006 | Quaid | A61B 90/37 600/424 |
| 2010/0170362 A1 | 7/2010 | Bennett et al. | |
| 2022/0409281 A1 | 12/2022 | Gormley et al. | |

* cited by examiner

SYSTEMS AND METHODS FOR SELECTIVELY ACTIVATING VIRTUAL GUIDE GEOMETRIES

CROSS-REFERENCE TO RELATED PATENT APPLICATIONS

This application is a continuation of U.S. application Ser. No. 18/198,424 filed May 17, 2023, which is a continuation of U.S. application Ser. No. 17/591,254 filed Feb. 2, 2022, which is a continuation of U.S. patent application Ser. No. 16/777,301 filed Jan. 30, 2020, which is a continuation of U.S. patent application Ser. No. 16/017,675 filed Jun. 25, 2018, which is a continuation of U.S. patent application Ser. No. 15/583,739 filed May 1, 2017, which is a continuation of U.S. patent application Ser. No. 13/340,668 filed Dec. 29, 2011, each of which is incorporated by reference herein in its entirety.

BACKGROUND

The present invention relates generally to haptic guidance systems and, more particularly, to systems and methods for selectively activating haptic guide zones.

Many surgical procedures require the use of specialized tools to perform surgical tasks with a high degree of accuracy and precision. In some cases, such surgical procedures require precise positioning and/or placement of the tool at or near a particular point within a patient's anatomy. For example, many orthopedic procedures rely on the accurate placement of pins, screws, guide and/or post holes, or other elements in a precise position and orientation with respect to an anatomical feature of the patient. In order to ensure that these elements are properly positioned and oriented, great care is required on the part of the surgeon to ensure that the surgical tool(s) (e.g., drill, saw, reamer, etc.) used to position these elements is precisely and accurately aligned with the anatomy of the patient. However, this can be particularly challenging without the use of a guide and even more challenging in minimally-invasive procedures where visibility at the surgical site is limited or, in some cases, nonexistent.

Early solutions for enhancing the accuracy and precision of the alignment of tools in a surgical environment involved the use of mechanical guide elements, such as jigs. These mechanical guides were typically placed and/or mounted in close proximity to the anatomy of the patient and provided a physical guide that maintained a desired position and orientation of the tool during its operation.

For example, some prosthetic implants used in knee joint replacement surgeries comprise projections, keels, and/or other mechanical elements that are configured to fit within corresponding holes or voids created in the bone to secure the implant to the bone. In order to ensure the accurate placement of these voids, a jig was often used to mechanically align a drill in a desired position and orientation with respect to the bone of a patient. During operation of the drill, the jig would maintain the desired orientation while the surgeon advanced the drill into to the bone until the desired depth was reached.

Although these guide jigs enhanced the accuracy and precision of the placement of voids within the bone, they needed to be physically installed in proximity to the bone during the surgical procedure. The accurate alignment and placement of these guides can take a considerable amount of time, which could prolong the surgical procedure. Furthermore, mechanical jigs and cutting guides are typically too large to fit within the relatively small spaces allowed for minimally-invasive procedures.

With the advent of computer-assisted surgery (CAS) systems, surgeons were no longer required to rely on mechanical jigs for precision positioning of surgical instruments. Specifically, many CAS systems include surgical navigation and tracking software that displays a graphical representation of the surgical site. Using the navigation and tracking features of the CAS system, the surgeon can view the location of a surgical instrument relative to the patient's anatomy. Using the graphical interface as a guide, the surgeon can manually navigate the surgical tool to a desired position within the surgical site.

More sophisticated CAS systems are configured for interactive coupling with the surgical tools. These CAS systems may be equipped with force feedback controls that provide the surgeon with haptic feedback when, for example, the surgical tool interacts with certain pre-established virtual boundaries. Such virtual boundaries may be established to constrain the surgical instrument from undesired interactions with certain areas of the patient's anatomy. By strategically arranging the virtual boundaries for the force feedback controls, users can create "virtual" guides that define the areas in which the tool can operate, as well as areas that prohibit tool operation. If a surgical procedure requires the drilling of a post hole in a patient's bone, a virtual boundary may be established to define the desired position, orientation, and size of the hole. The virtual boundary may constrain a surgical tool from operating outside of the established boundary.

Although existing virtual guide methods provide a solution for defining the areas of allowed operation (and corresponding areas of constrained operation) of a surgical instrument, they may still be inefficient. For example, conventional virtual guide methods do include a solution for aligning a surgical tool in a proper orientation prior to engagement with the patient's anatomy. As a result, in surgical procedures that require precision cuts having specific orientations (such as the drilling of post or guide holes within bone), the surgeon may be required to manually "search" for the appropriate orientation by using the tip of the surgical tool as an exploring device to first locate the engagement point at the surface of the patient's bone. Once the engagement point has been located, the surgeon then manually pivots the surgical tool to locate the appropriate orientation for advancing the tool to the target point. Not only is such a manual process frustrating to the surgeon, it may unnecessarily prolong the surgery, which can increase costs.

Moreover, existing CAS systems may not provide an effective solution for enabling and disabling haptic zones during the performance of a surgical procedure. This is particularly problematic in situations in which multiple haptic boundaries are located in close proximity with (or overlap) one another. In such situations, the haptic boundaries may provide conflicting haptic feedback, constraining movement of the surgical instrument in an undesirable or unintended manner. For example, in situations in which haptic zones overlap, a first haptic zone may constrain movement of the surgical instrument in one direction, while a second haptic zone may constrain movement of the surgical instrument in the opposite direction. As a result, movement of the surgical instrument may be severely limited by the conflicting haptic feedback imposed on the instrument by the first and second haptic zones. It may therefore be advantageous to provide a solution for selectively or sequentially activating individual haptic guide zones to limit the possibility of conflicts between overlapping haptic zones.

The presently disclosed systems and methods for selectively activating haptic guide zones are directed to overcoming one or more of the problems set forth above and/or other problems in the art.

SUMMARY OF THE INVENTION

According to one aspect, the present disclosure is directed to a method for activating a virtual haptic geometry based on a position of a portion of an instrument relative to a target point. The method comprises detecting a presence of a reference point of an instrument within a threshold distance of a target point. A virtual haptic geometry corresponding to the target point may be activated in response to the detected presence of the reference point of the instrument within the threshold distance.

In accordance with another aspect, the present disclosure is directed to a computer-implemented method for activating a virtual haptic geometry. The method may include determining, by a processor associated with a computer, a position of a reference point of an instrument. A distance between the reference point and each of a plurality of target points may be determined by the processor. The method may also include identifying, by the processor, the target point that is closest to the reference point, and activating a virtual haptic geometry associated with the identified target point.

According to another aspect, the present disclosure is directed to a method for activating a virtual haptic geometry. The method may include identifying a plurality of open target points associated with a surgical environment, and determining a position of a reference point of a surgical instrument relative to each of the identified open target points. The method may include identifying a first open target point that is closest to the reference point, and activating a virtual haptic geometry associated with the first open target point that is closest to the reference point. A position of the reference point may be monitored and, after determining that the reference point has reached the first open target point, the virtual haptic geometry may be deactivated.

In accordance with yet another aspect, the present disclosure is directed to a computer-assisted surgery system comprising a surgical instrument for performing at least one task associated with a surgical procedure and a processor, operatively coupled to the surgical instrument. The processor may be configured to detect a presence of a reference point of the surgical instrument within a threshold distance of a target point. A virtual haptic geometry corresponding to the target point may be activated based on the detected presence of the reference point of the instrument.

According to yet another aspect, the present disclosure is directed to computer-implemented method for activating a virtual haptic geometry. The method may also comprise displaying, by a processor on a display associated with a computer, a plurality of target points. A virtual haptic geometry associated with one target point of the plurality of target points may be activated based, at least in part, on a user selection of the one target point from among the plurality of target points.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or similar parts.

Figure 1:
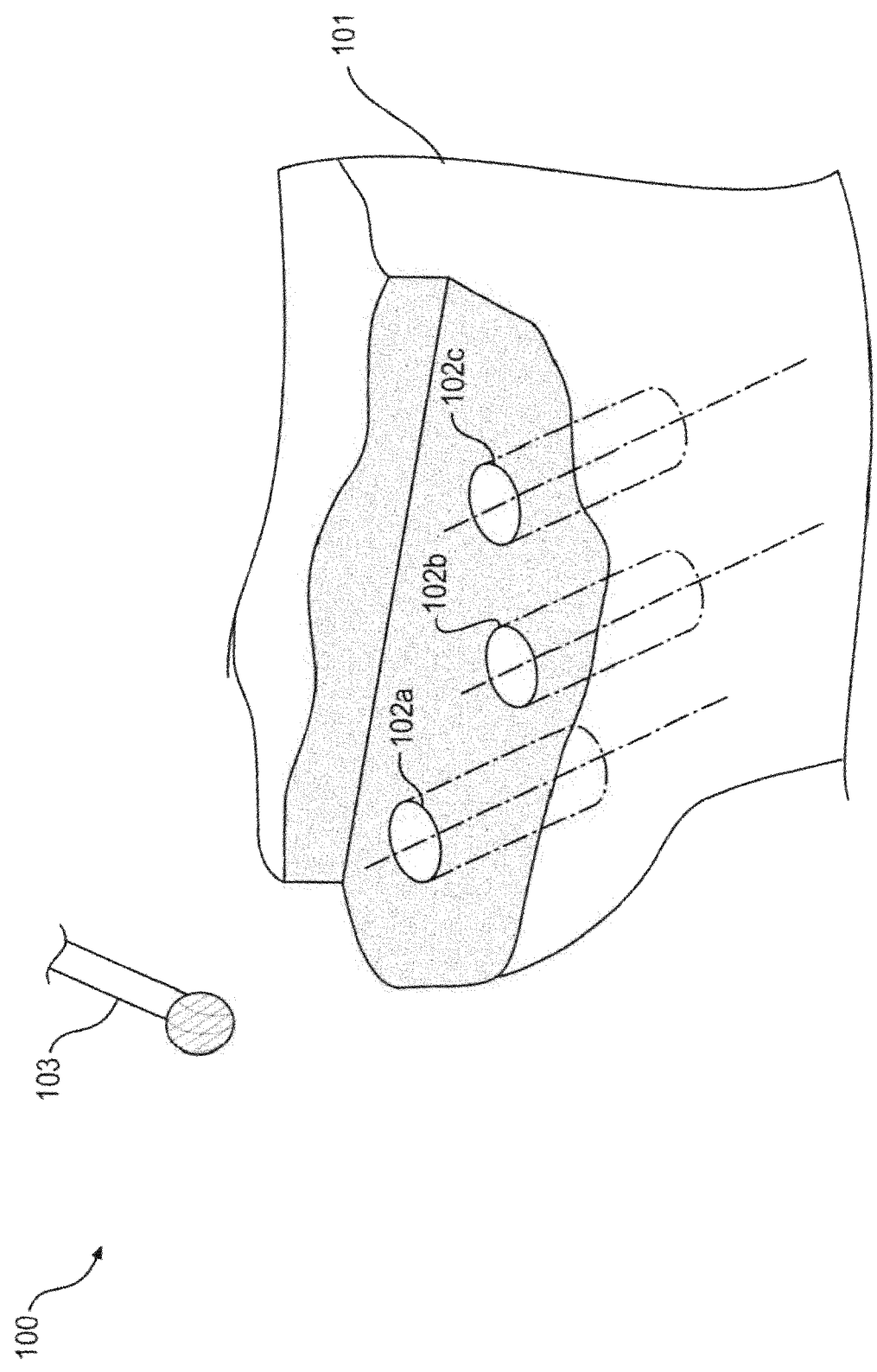
FIG. 1 provides a perspective view of an exemplary surgical environment in which systems and methods consistent with the disclosed embodiments may be employed.

FIG. 1 illustrates an exemplary surgical environment 100 in which processes and methods consistent with the disclosed embodiments may be employed. As illustrated in FIG. 1, many surgical procedures, such as knee replacement procedures, require accurate and precise modification to the patient's anatomy. One such example is the placement of post or guide holes 102a-102c within a patient's tibia 101 using a surgical instrument, such as drill (not shown), having a rotary cutting tool 103. Because these post or guide holes 102a-102c correspond to projections on a prefabricated prosthetic implant (not shown), each hole should be accurately and precisely placed at a specific location, depth, and orientation within the patient's bone.

In order to ensure efficient and proper alignment of the post holes within the patient's anatomy, a computer-aided surgery (CAS) system may be used to generate a graphical representation of the surgical site and a corresponding virtual guide that may aid the surgeon in properly aligning the tool prior to interaction with patient's anatomy. The CAS system consistent with the present disclosure may also provide a haptic feedback geometry that captures the surgical tool while the tool approaches the engagement site. Once captured, the boundaries of the virtual haptic geometry may limit or restrict the movement of the surgical instrument within the confines of a haptic volume defined by the virtual haptic geometry. Based on the surgeon's movements, the haptic volume may be gradually reduced, limiting the range of motion of the surgical instrument until the surgical tool is aligned with the target access associated with the post holes. Systems and methods for aligning the surgical instrument consistent with the disclosed embodiments are discussed in greater detail below and in the accompanying drawings.

As explained, many CAS systems include software that allows users to electronically register certain anatomic features (e.g., bones, soft tissues, etc.), surgical instruments, and other landmarks associated with the surgical site. CAS systems may generate a graphical representation of the surgical site based on the registration of the anatomic features. The CAS software also allows users to plan certain aspects of the surgical procedure, and register these aspects for display with the graphical representation of the surgical site. For example, in a knee joint replacement procedure, a surgeon may register target navigation points, the location and depth of bone and tissue cuts, virtual boundaries that may be associated with a corresponding reference for the application of haptic force, and other aspects of the surgery.

Figure 2:
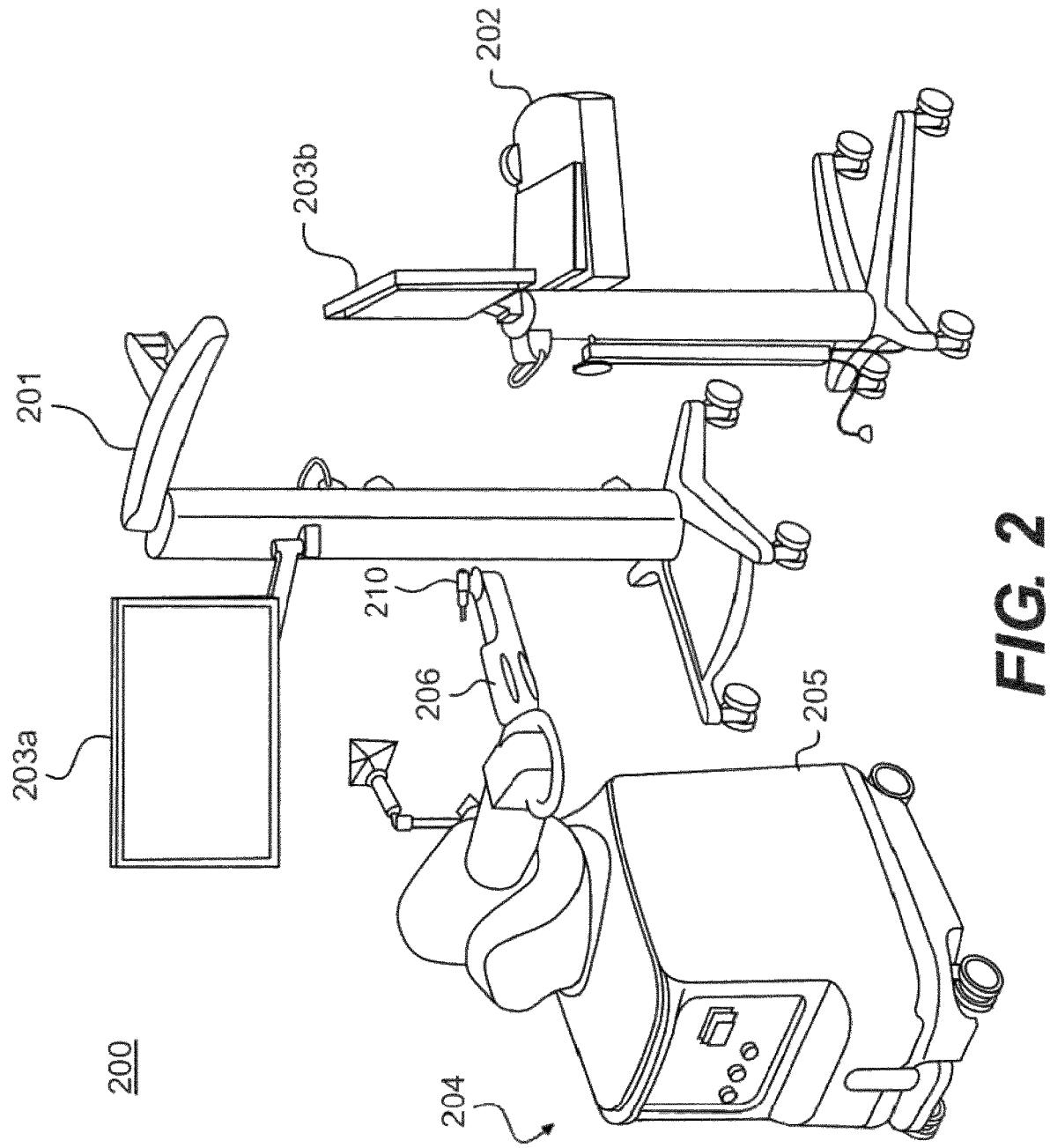
FIG. 2 provides a schematic illustration of an exemplary computer-assisted surgery (CAS) system, in which certain methods consistent with the disclosed embodiments may be implemented.

FIG. 2 provides a schematic diagram of an exemplary computer-assisted surgery (CAS) system 200, in which processes and features associated with certain disclosed embodiments may be implemented. CAS system 200 may be configured to perform a wide variety of orthopedic surgical procedures such as, for example, partial or total joint replacement surgeries. As illustrated in FIG. 2, CAS system 200 may comprise a tracking system 201, computer-assisted navigation system 202, one or more display devices 203a, 203b, and a robotic arm 204. It should be appreciated that CAS system 200, as well as the methods and processes described herein, may be applicable to many different types of joint replacement procedures. Although certain disclosed embodiments may be described with respect to knee replacement procedures, the concepts and methods described herein may be applicable to other types of orthopedic surgeries, such as partial hip replacement, full or partial hip resurfacing, shoulder replacement or resurfacing procedures, and other types of orthopedic procedures.

Robotic arm 204 can be used in an interactive manner by a surgeon to perform a surgical procedure, such as a knee replacement procedure, on a patient. As shown in FIG. 2, robotic arm 204 includes a base 205, an articulated arm 206, a force system (not shown), and a controller (not shown). A surgical tool 210 (e.g., an end effector having an operating member, such as a saw, reamer, or burr) may be coupled to the articulated arm 206. The surgeon can manipulate the surgical tool 210 by grasping and manually moving the articulated arm 206 and/or the surgical tool 210.

The force system and controller are configured to provide control or guidance to the surgeon during manipulation of the surgical tool. The force system is configured to provide at least some force to the surgical tool via the articulated arm 206, and the controller is programmed to generate control signals for controlling the force system. In one embodiment, the force system includes actuators and a backdriveable transmission that provide haptic (or force) feedback to constrain or inhibit the surgeon from manually moving the surgical tool beyond predefined virtual boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. According to one embodiment, CAS system 200 is the RIO® Robotic Arm Interactive Orthopedic System manufactured by MAKO Surgical Corp. of Fort Lauderdale Florida. The force system and controller may be housed within the robotic arm 204.

Tracking system 201 may include any suitable device or system configured to track the relative locations, positions, orientations, and/or poses of the surgical tool 210 (coupled to robotic arm 204) and/or positions of registered portions of a patient's anatomy, such as bones. Such devices may employ optical, mechanical, or electromagnetic pose tracking technologies. According to one embodiment, tracking system 201 may comprise a vision-based pose tracking technology, wherein an optical detector, such as a camera or infrared sensor, is configured to determine the position of one or more optical transponders (not shown). Based on the position of the optical transponders, tracking system 201 may capture the pose (i.e., the position and orientation) information of a portion of the patient's anatomy that is registered to that transponder or set of transponders.

Navigation system 202 may be communicatively coupled to tracking system 201 and may be configured to receive tracking data from tracking system 201. Based on the received tracking data, navigation system 202 may determine the position and orientation associated with one or more registered features of the surgical environment, such as surgical tool 210 or portions of the patient's anatomy. Navigation system 202 may also include surgical planning and surgical assistance software that may be used by a surgeon or surgical support staff during the surgical procedure. For example, during a joint replacement procedure, navigation system 202 may display images related to the surgical procedure on one or both of the display devices 203a, 203b.

Figure 3:
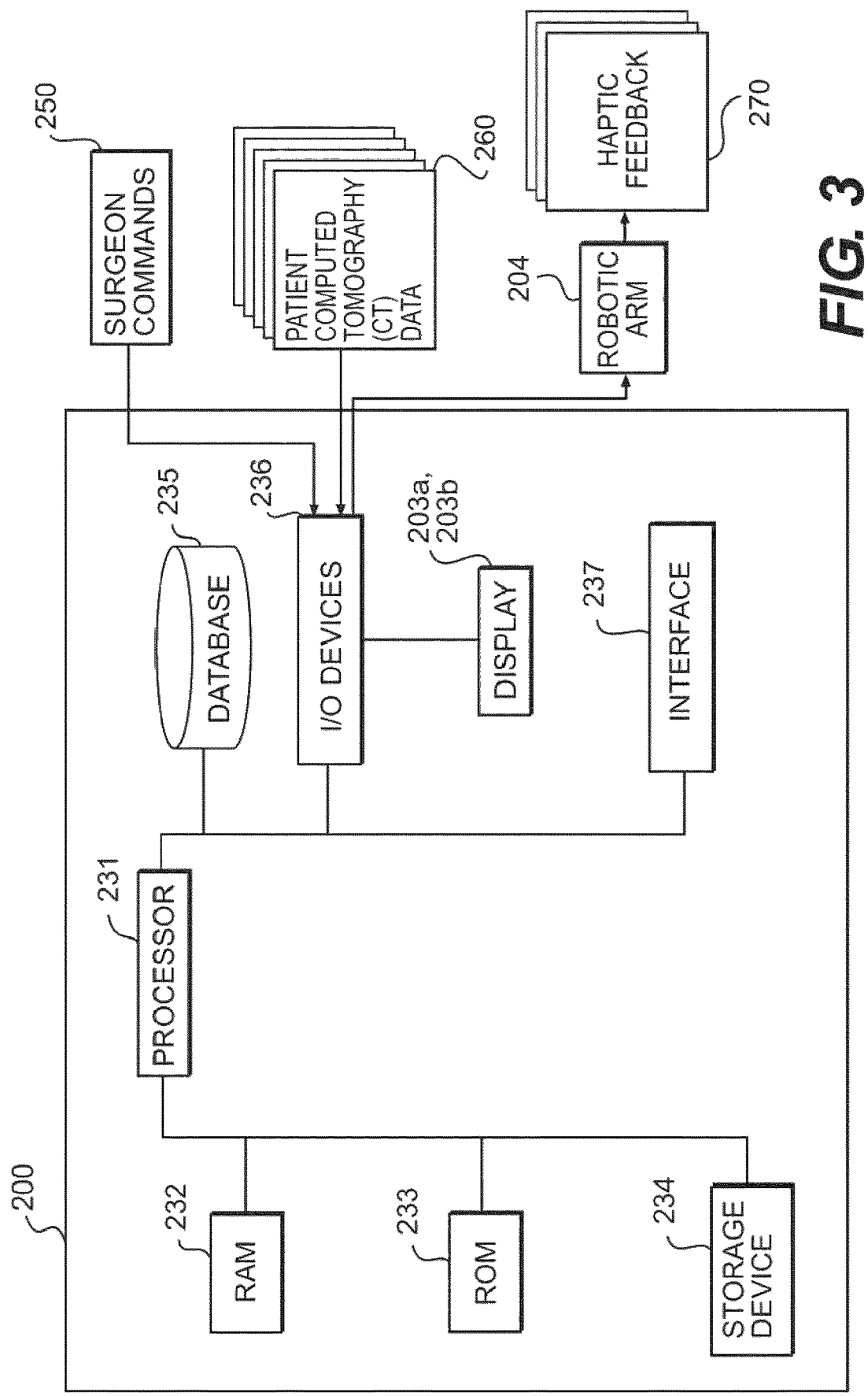
FIG. 3 provides a schematic diagram of an exemplary computer system, which may be used in one or more components associated with the CAS system illustrated in FIG. 2.

Navigation system 202 (and/or one or more constituent components of CAS system 200) may include or embody a processor-based system (such as a general or special-purpose computer) in which processes and methods consistent with the disclosed embodiments may be implemented. For example, as illustrated in FIG. 3, CAS system 200 may include one or more hardware and/or software components configured to execute software programs, such as, tracking software, surgical navigation software, 3-D bone modeling or imaging software, and/or software for establishing and modifying virtual haptic boundaries for use with a force system to provide haptic feedback to surgical tool 210. For example, CAS system 200 may include one or more hardware components such as, for example, a central processing unit (CPU) (processor 231); computer-readable media, such as a random access memory (RAM) module 232, a read-only memory (ROM) module 233, and a storage device 234; a database 235; one or more input/output (I/O) devices 236; and a network interface 237. The computer system associated with CAS system 200 may include additional, fewer, and/or different components than those listed above. It is understood that the components listed above are exemplary only and not intended to be limiting.

Processor 231 may include one or more microprocessors, each configured to execute instructions and process data to perform one or more functions associated with CAS system 200. As illustrated in FIG. 2, processor 231 may be communicatively coupled to RAM 232, ROM 233, storage device 234, database 235, I/O devices 236, and network interface 237. Processor 231 may be configured to execute sequences of computer program instructions to perform various processes, which will be described in detail below. The computer program instructions may be loaded into RAM for execution by processor 231.

Computer-readable media, such as RAM 232, ROM 233, and storage device 234, may be configured to store computer-readable instructions that, when executed by processor 231, may cause CAS system 200 or one or more constituent components, such as navigation system 202, to perform functions or tasks associated with CAS system 200. For example, computer readable media may include instructions for causing the CAS system 200 to perform one or more methods for determining changes in parameters of a hip joint after a hip arthroplasty procedure. Computer-readable media may also contain instructions that cause tracking system 201 to capture positions of a plurality of anatomical landmarks associated with certain registered objects, such as surgical tool 210 or portions of a patient's anatomy, and cause navigation system 202 to generate virtual representations of the registered objects for display on I/O devices 236. Exemplary methods for which computer-readable media may contain instructions will be described in greater detail below. It is contemplated that each portion of a method described herein may have corresponding instructions stored in computer-readable media for causing one or more components of CAS system 200 to perform the method described.

I/O devices 236 may include one or more components configured to communicate information with a user associated with CAS system 200. For example, I/O devices 236 may include a console with an integrated keyboard and mouse to allow a user (e.g., a surgeon) to input parameters (e.g., surgeon commands 250) associated with CAS system 200. I/O devices 236 may also include a display, such as monitors 203a, 203b, including a graphical user interface (GUI) for outputting information on a monitor. I/O devices 236 may also include peripheral devices such as, for example, a printer for printing: information associated with CAS system 236, a user-accessible disk drive (e.g., a USB port, a floppy, CD-ROM, or DVD-ROM drive, etc.) to allow a user to input data stored on a portable media device, a microphone, a speaker system, or any other suitable type of interface device. For example, I/O devices 236 may include an electronic interface that allows a user to input patient computed tomography (CT) data 260 into CAS system 200. This CT data may then be used to generate and manipulate virtual representations of portions of the patient's anatomy (e.g., bones) in software.

Processor 231 associated with CAS system 200 may be configured to establish a virtual haptic geometry associated with or relative to one or more features of a patient's anatomy. As explained, CAS system 200 may be configured to create a virtual representation of a surgical site that includes, for example, virtual representations of a patient's anatomy, a surgical instrument to be used during a surgical procedure, a probe tool for registering other objects within the surgical site, and any other such object associated with a surgical site.

In addition to physical objects, CAS system 200 may be configured to generate virtual objects—objects that exist in software, and which may be useful during the performance of a surgical procedure. For example, CAS system 200 may be configured to generate virtual boundaries that correspond to a surgeon's plan for preparing a bone, such as boundaries defining areas of the bone that the surgeon plans to cut, remove, or otherwise alter. Alternatively or additionally, CAS system 200 may define virtual objects that correspond to a desired path or course over which a portion of surgical tool 210 should navigate to perform a particular task.

Figure 4:
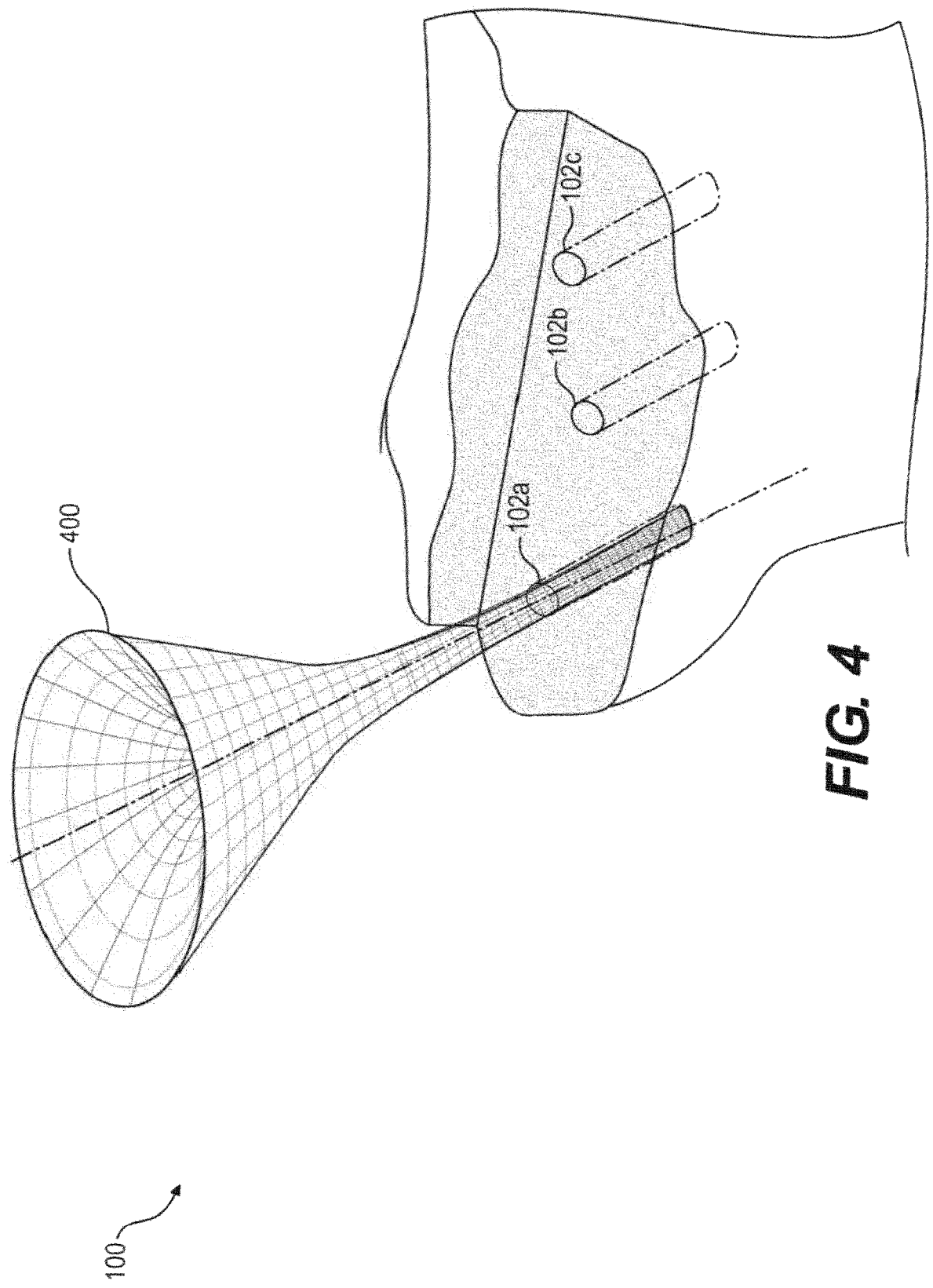
FIG. 4 provides an illustration of an exemplary virtual haptic volume, consistent with certain disclosed embodiments.
Figure 5:
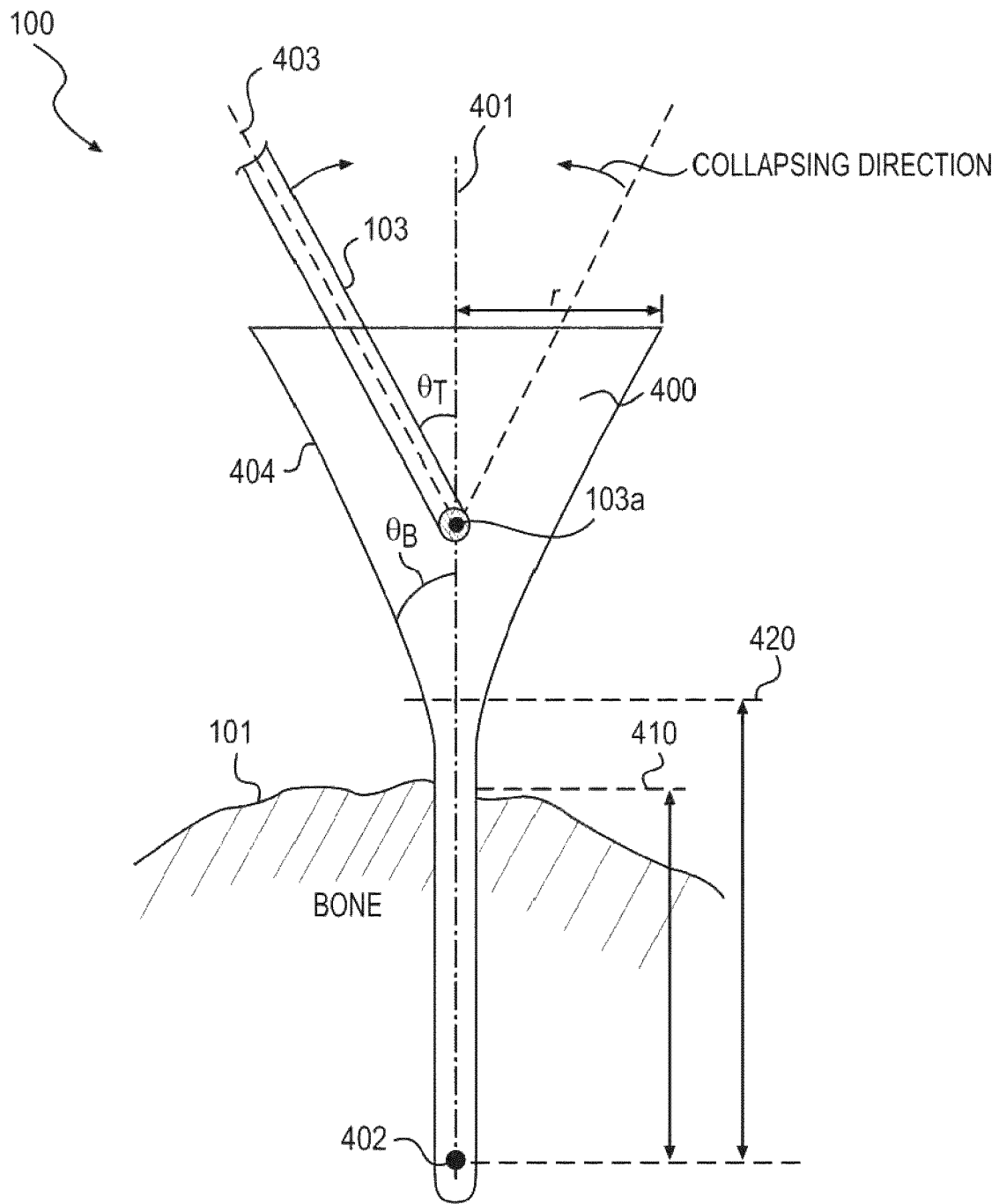
FIG. 5 provides a 2-dimensional side view of a virtual haptic volume, consistent with the disclosed embodiments.

According to one embodiment, CAS system 200 may be configured to generate a virtual haptic geometry that defines a point, line, surface, or volume in a virtual coordinate space. The virtual haptic geometry may be associated with a haptic feedback or force system of CAS system 200 such that, when a tracked position of a portion of the surgical tool (e.g., an established center point 103a or tool axis 403 of cutting tool 103) interacts with the virtual haptic geometry, a haptic feedback is generated and applied to surgical tool 210. FIGS. 4 and 5 provide alternate views of an exemplary virtual haptic geometry 400 that may be generated consistent with the presently disclosed embodiments.

According to one exemplary embodiment, and as illustrated in FIG. 4, virtual haptic geometry 400 may be a substantially funnel-shaped volume that is positioned and oriented relative to a patient's anatomy, such as femur 101. As such, virtual haptic geometry 400 may define a virtual pathway to quickly and efficiently guide and position a surgical instrument, such as rotary drill or burr, into a proper alignment relative to femur 101 prior to engagement with femur 101. According to the embodiment illustrated in FIG. 4, virtual haptic geometry may comprise a substantially cone-shaped portion that converges toward a substantially cylindrically-shaped portion. The cylindrically-shaped portion may extend toward a target end point (402 in FIG. 5), which, in the example illustrated in FIG. 4, corresponds to the depth of post holes 102.

Figure 8:
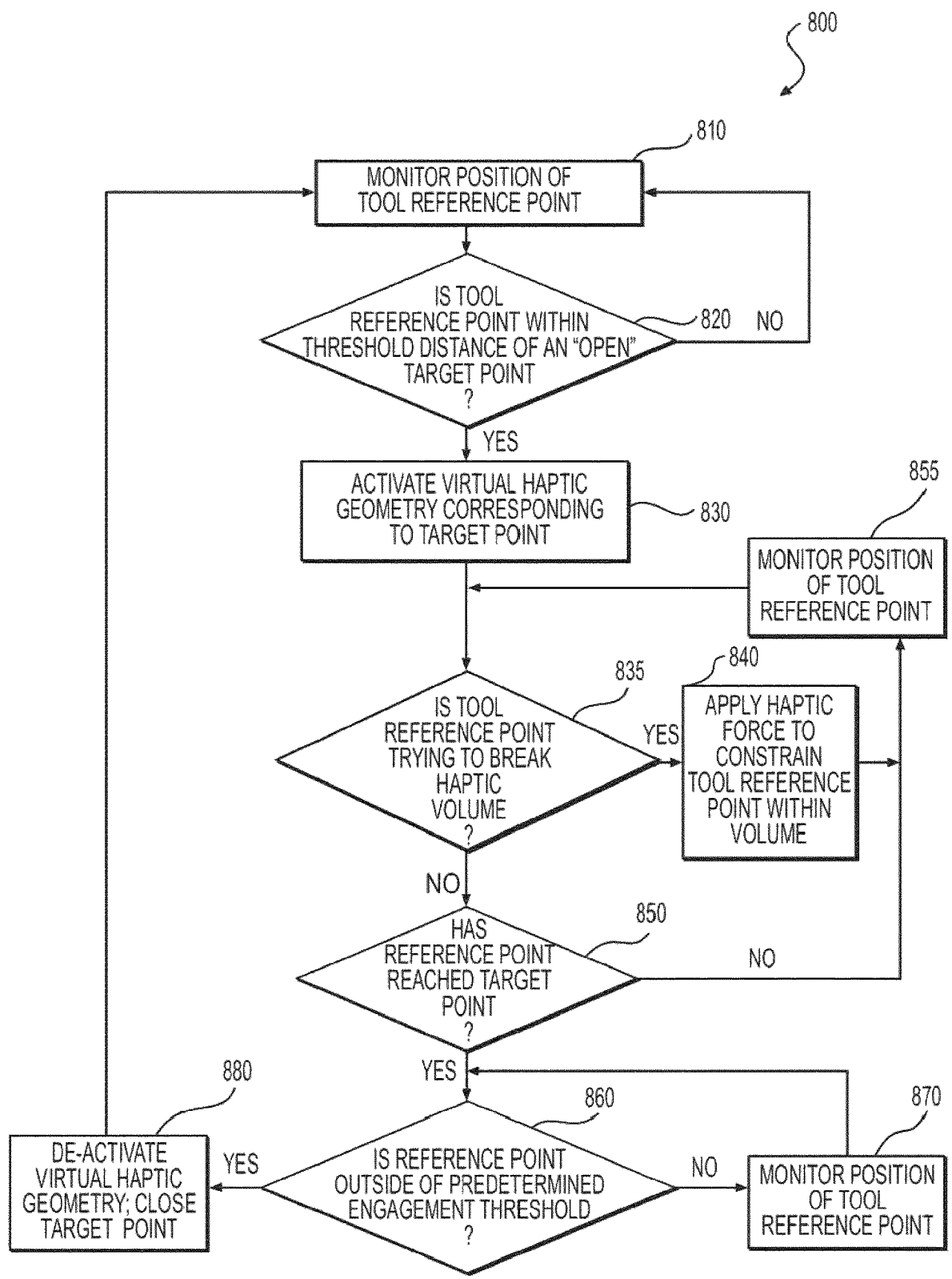
FIG. 8 provides a flowchart depicting an exemplary method for selectively activating a haptic guide zone, consistent with the disclosed embodiments.

FIG. 5 illustrates a side view of the exemplary virtual haptic geometry 400 shown in FIG. 4, being accessed by cutting tool 103. As illustrated in FIG. 5, virtual haptic geometry 400 may be defined about a target axis 401 that includes a target end point 402. Virtual haptic geometry 400 may comprise a boundary surface 404, which may be positioned at an initial boundary angle, $\theta_\beta$, relative to the target axis 401. According to the embodiment shown in FIG. 5, boundary surface 404 may define a substantially cone-shaped volume having an initial base radius, r. It should be noted, however, that, although the upper portion of virtual haptic geometry 400 is illustrated in certain embodiments as having a substantially cone-shaped boundary surface, it is contemplated that virtual haptic geometry 400 may include or embody any shape suitable for guiding a cutting tool 103 toward a target end point 402. For example, as shown in FIG. 8, boundary surface 404 may define a substantially curved upper portion, which is designed to converge toward the target axis more aggressively than the substantially linear boundary surface shown in FIG. 5.

Target end point 402 may be a user-defined point that corresponds to the target destination of at least a portion of cutting tool 103. According to one embodiment, target end point 402 may define a target depth 410 of post or guide hole 102 of femur 101. As such, target end point 402 corresponds to a desired depth 410 that a reference point 103a of tool 103 (also referred to herein as a tool center point (TCP)) can reach before a haptic feedback force is applied to surgical tool 210.

Target axis 401 may include target end point 402 and may serve as a central axis about which virtual haptic geometry 400 may be defined. Target axis 401 may also define a desired axis for approaching target end point 402 with cutting tool 103. As such, target axis 401 may define the axis to which virtual haptic geometry 400 converges, and may correspond to the desired or ideal orientation of approach of surgical tool 403 toward target end point 402.

During operation of CAS system 200 and in accordance with an exemplary embodiment, virtual haptic geometry 400 becomes associated with cutting tool 103 when reference point 103a of cutting tool 103 enters the volume defined by virtual haptic geometry. Once active, virtual haptic geometry 400 may be configured to provide a haptic feedback when cutting tool 103 interacts with one or more virtual boundaries 404. For example, virtual haptic geometry 400 may define a haptic "wall" that constrains, inhibits, or prevents cutting tool 103 and/or reference point 103a from moving beyond the boundary surface 404 of virtual haptic surface 400. In an exemplary embodiment, virtual haptic geometry 400 may be configured with an "opening" for allowing cutting tool 103 to disengage from virtual haptic geometry 400. While this disengagement opening may be located anywhere along virtual haptic geometry 400, an exemplary embodiment includes the opening along the surface of virtual haptic geometry 404 that is located farthest from bone or tissue surfaces of the patient. In the embodiment illustrated in FIG. 5, the top surface of boundary surface 404 may be configured as the disengagement opening.

As an alternative or in addition to constraining the movement of cutting tool 103 (and/or tool reference point 103a) to within the volume defined by virtual haptic geometry 400, CAS system 200 may be configured to guide cutting tool 103 toward a desired orientation prior to engagement with femur 101. Specifically, CAS system 200 may be configured to monitor a tool orientation angle, $\theta_T$, which comprises the angle between the tool axis 403 and a target axis 401. As will be explained in further detail below, CAS system 200 may be configured to facilitate alignment of the tool axis 403 with target axis 401 by modifying the location of boundary surface 404 of virtual haptic geometry 400 based on the location of tool axis 403.

To ensure that cutting tool is positioned in the proper orientation prior to engagement with a surface of the patient's anatomy, an intermediate haptic threshold may be established and associated with virtual haptic boundary 400. Specifically, the virtual haptic boundary 400 may include an intermediate tool stop haptic plane 420 that provides haptic feedback if reference point 103a attempts to advance without being in the proper orientation. The haptic feedback may include a haptic wall that constrains advancement of cutting tool 103 past intermediate tool stop haptic plane 420 if one or more of tool axis 403 and/or tool reference point 103a is not aligned with target axis 401.

As explained, software associated with CAS system 200 may be configured to register and track certain aspects of surgical environment 100. For example, cutting tool 103, along with other features of surgical environment 100, may be registered and associated with a virtual coordinate space for tracking and display by CAS system 200. As such, tracking system 201 of CAS system 200 can determine the relative position and orientation of cutting tool 103 in the virtual coordinate space.

In order to properly monitor the orientation of tool axis 403 of cutting tool 103, the tool axis 403 of cutting tool 103 should first be registered for tracking in virtual coordinate space of CAS system 200. According to one embodiment (such as that illustrated in FIG. 5), tool axis 403 may correspond to the central axis of a rotary burr, which passes through reference point 103a associated with the center of the tip of the rotary burr. Tool axis 403, along with reference point 103a, may be determined during a calibration process of CAS system 200, prior to the surgical procedure. Alternatively or additionally, CAS system 200 may be registered as part of the registration process during the surgical procedure by using a pre-calibrated registration probe to capture and record the locations of a plurality of points along tool axis 403. Because the position of the axis at the surface of the cylindrically-shaped rotary burr is slightly different than the position of the axis at the true center of tool axis 403, CAS system 200 may be provided with an offset to project the tool axis 403 to the center of cutting tool 103.

According to yet another embodiment, the pre-calibrated registration probe may be used to capture a large number of points along the surface of cutting tool 103. Based on the relative locations of these points, software associated with CAS system 200 may be configured to derive tool axis 403. It is contemplated that additional and/or different methods may be used for registering various aspects of cutting tool 103 than those that are listed above. For example, a virtual software model representing cutting tool 103 may be generated using computed tomography (CT) scan information. The model may be registered in the virtual coordinate space using the calibrated registration probe. Once registered, tracking system 201 associated with CAS system 200 can monitor the real-time location, position, and orientation of registered components of surgical environment 100 relative to the established virtual coordinate space in order to guide cutting tool 103 to, target end points 402a-402c by sequentially activating each of target end points 402a-402c in accordance with the processes and methods consistent with the disclosed embodiments.

Figure 6:
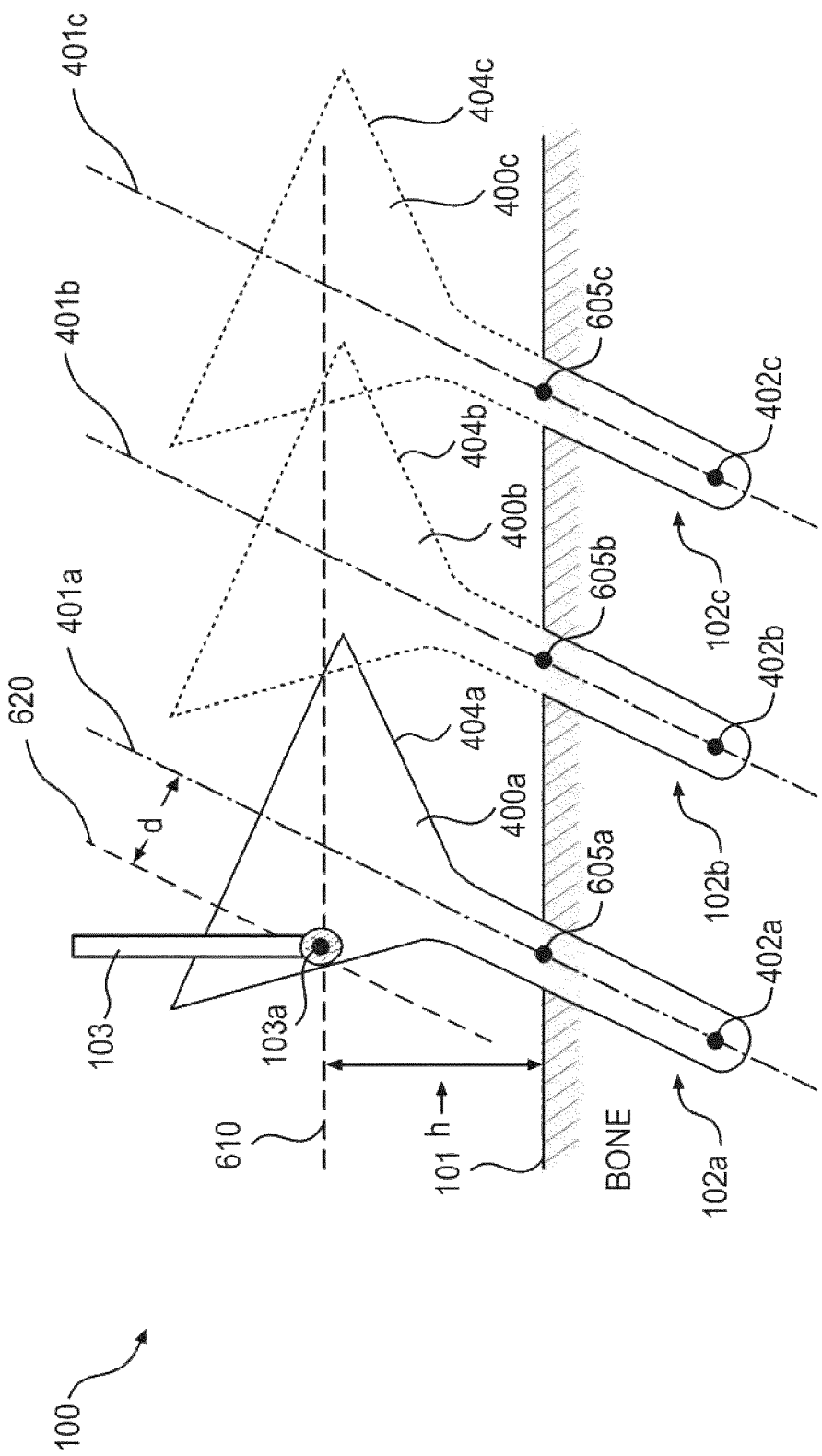
FIG. 6 provides a side view of an exemplary surgical environment having a plurality of target points, which may be selectively activated using the systems and methods consistent with certain disclosed embodiments.

FIG. 6 illustrates a surgical environment 100 having a plurality of target end points 402a-402c, each of which is associated with a respective virtual haptic geometry 400a-400c for guiding a cutting tool 103 toward target end points 402a-402c, respectively. As illustrated in FIG. 6, portions of virtual haptic geometries 400a-400c may overlap with one another. If each of virtual haptic geometries 400a-400c are "active" at the same time, haptic forces associated with one virtual haptic geometry 400a may interfere with one or more of haptic forces associated virtual haptic geometries 400b, 400c, particularly if cutting tool 103 is located in one of the overlapping regions associated with virtual haptic geometries 400a-400c. As such, processes consistent with the disclosed embodiments provide a solution for selectively activating one of virtual haptic geometries 400a-400c at a time.

FIG. 6 illustrates an embodiment in which a first virtual haptic geometry 400a is selectively "activated," while the remaining virtual haptic geometries 400b, 400c are maintained in an inactive state. As such, only haptic forces associated with active virtual haptic geometry 400a are operable as the haptic guide zone for guiding reference point 103a of cutting tool 103 toward target end point 402a associated with active virtual haptic geometry 400a. The remaining haptic zones are selectively and/or sequentially activated once the task associated with virtual haptic geometry 400a is completed, unless and until the active virtual haptic geometry 400a is deactivated.

According to one embodiment, virtual haptic geometry 400a is automatically activated when cutting tool 103 (and/or reference point 103a) is positioned within a threshold distance of target end point 402a associated with virtual haptic geometry 400a. For example, software associated with CAS system 200 may be configured to track the position of a reference point 103a of cutting tool 103 relative to target end points 402a-402c. CAS system 200 may determine which of target end point 402a-402c is closest to reference point 103a of cutting tool 103, and activate the corresponding virtual haptic geometry 400a associated with the closest target end point 402a.

It is contemplated that additional and/or different criteria may be used for selectively activating virtual haptic geometries 400a-400c. For example, CAS system 200 may be configured to selectively activate virtual haptic geometries 400a-400c when reference point 103a of cutting tool 103 enters a volume associated with one of virtual haptic geometries 400a-400c. Alternatively or additionally, CAS system 200 may be configured to selectively activate one or more of virtual haptic geometries 400a-400c when reference point 103a is within the threshold engagement area associated with one of virtual haptic geometries 400a-400c. The engagement area may be defined by an engagement height, h, (measured from a surface of tibia 101 to a predetermined height threshold 610) and an engagement distance, d, (measured from target axis 401a to a predetermined distance threshold 620).

According to one exemplary embodiment, CAS system 200 activates virtual haptic geometry 400a when reference point 103a of cutting tool 103 is within both (1) the volume defined by virtual haptic geometry 400a and (2) the threshold engagement area. By providing multiple criteria for selectively activating one virtual haptic geometry (e.g., virtual haptic geometry 400a) from among a plurality of virtual haptic geometries 400a-400c, CAS system 200 may be configured to prevent "accidental" activation of a virtual haptic geometry 400a-400c that can result from using a single criterion for selectively activating virtual haptic geometries 400a-400c.

As an alternative or in addition to selectively activating virtual haptic geometry 400a based on a position of cutting tool 103 relative to target end point 402a, virtual haptic geometries 400a-400c may be activated manually, based on a user selection using a graphical user interface associated with CAS system 200. That is, a user of CAS system 200 may selectively activate virtual haptic geometry 400a from among available or "open" virtual haptic geometries 400a-400c. According to one embodiment, the manual activation technique can be implemented in addition to the automatic activation technique described above. For example, CAS system 200 may be configured to automatically activate virtual haptic boundaries 400a-400c based on the tracked position of reference point 103a of cutting tool 103, as described above. However, the manual activation technique may be available to the user on an ad-hoc basis, allowing a user of CAS system 200 to selectively manually override the automatic activation technique.

Processes and methods consistent with the disclosed embodiments provide a solution for quickly and efficiently guiding cutting tool 103 to a proper orientation for engagement with a patient's anatomy. Exemplary methods consistent with the disclosed embodiments track the position and orientation of tool axis 403 relative to a target axis 401. As the orientation angle, $\theta_T$, between tool axis 403 and target axis 401 becomes smaller, virtual haptic geometry 400 associated with surgical tool 210 is repositioned behind the virtual representation of cutting tool 103, creating a boundary surface that "collapses" as cutting tool 103 is brought into alignment with target axis 401. As a result, cutting tool 103 is constrained from being rotated to an angle that is greater than the smallest orientation angle. This "collapsing" virtual haptic geometry effectively allows the surgeon the freedom to move or rotate cutting tool 103 only to those positions that bring cutting tool 103 in closer alignment with target axis 401. Eventually, as the surgeon rotates cutting tool 103 within the area defined by virtual haptic geometry 400, the boundary decreases in size until tool axis 403 is sufficiently aligned with target axis 401.

In addition, processes and methods consistent with the disclosed embodiments provide a solution for selectively (and sequentially) activating haptic guide zones to limit the potential for interference between adjacent or overlapping haptic guide zones. Accordingly, systems and methods consistent with certain disclosed embodiments provide a solution for selectively activating haptic guides zones based on the proximity of cutting tool 103 to a target point (such as target end point 402a-402c or an engagement point 605a-605c). In accordance with an exemplary embodiment, haptic zones that are not activated remain inactive. Consequently, corresponding haptic forces associated with inactive haptic zones will be disabled and prevented from operating on cutting tool 103.

Alternatively or additionally, certain processes and methods consistent with the disclosed embodiments provide a feature that allows a user to select, via a graphical user interface, one haptic zone from a plurality of available haptic zones that is to be activated. The unselected haptic zones may remain inactive, at least until the task associated with the haptic zone has been completed or until the user otherwise deactivates the virtual haptic geometry (by, for example, exiting the virtual haptic geometry).

Figure 7:
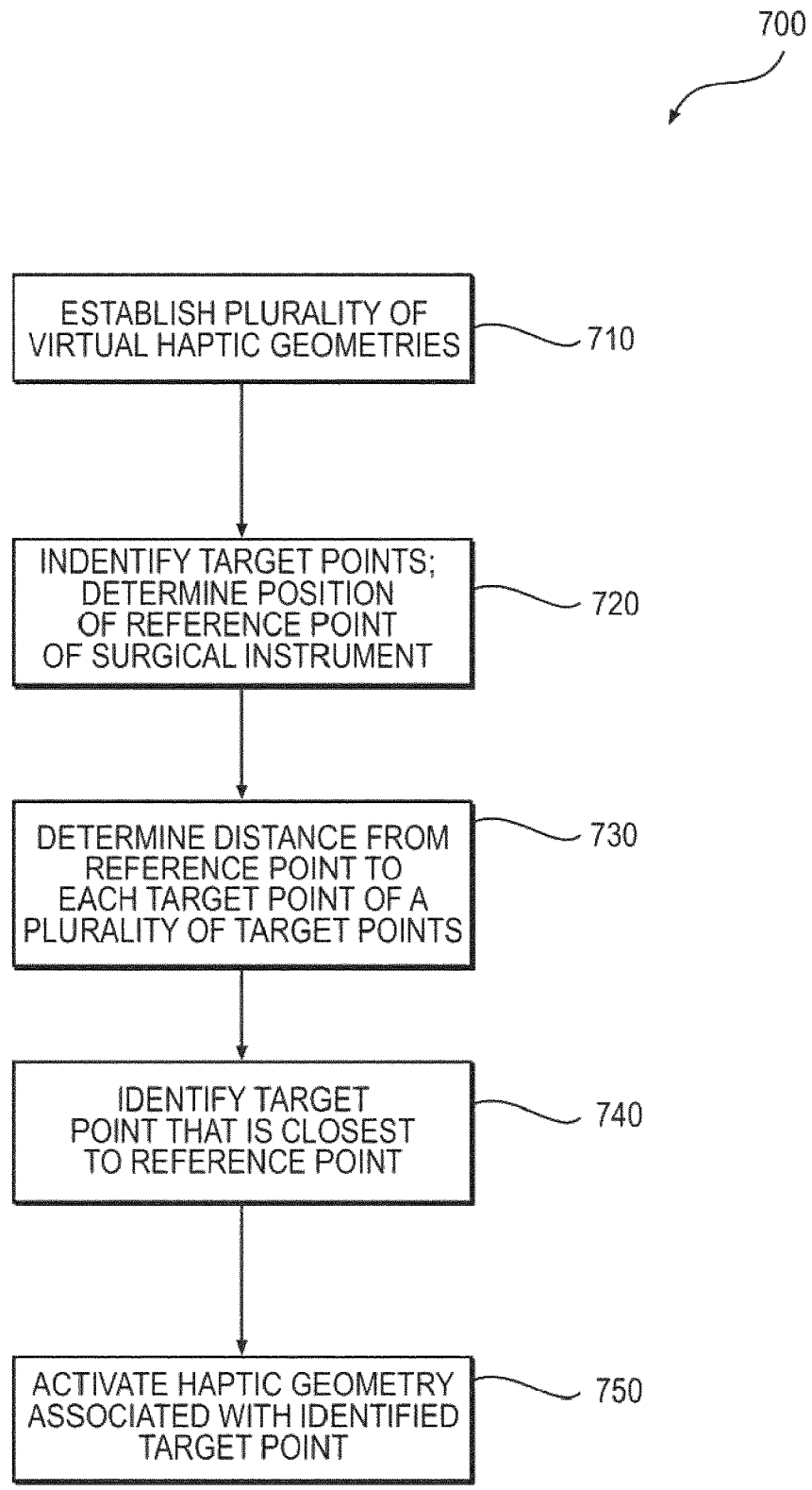
FIG. 7 provides a flowchart depicting an exemplary method for activating a haptic guide zone, consistent with certain disclosed embodiments.

FIG. 7 provides a flowchart 700 illustrating an exemplary method for selectively activating a virtual haptic geometry based on the position of cutting tool 103 relative to surgical environment 100. As illustrated in FIG. 7, the process may involve establishing a plurality of virtual haptic geometries 400a-400c for aiding in the guidance of cutting tool 103 (and/or reference point 103a associated therewith) to target point(s) 402a-402c (Step 710). For example, during a planning phase of surgical procedure that involves the preparation of a bone for receiving a prosthetic implant, a user of CAS system 200 may plan the areas of the bone that require resection. In some situations, the implant includes a plurality of stabilizing projections (not shown) that are designed to fit within corresponding post holes created in the bone. During the surgical planning process, the user of CAS system 200 may plan the location, depth, and orientation of post holes 102a-102c that are to be resected in order to receive the corresponding projections of the implant. The user may also specify target end point(s) 402a-402c, which defines the location that reference point 103a of cutting tool 103 should reach to meet the target depth parameter. The user may also specify target axes 401a-401c, which define the proper approach orientation of cutting tool 103 to achieve the desired orientation of respective post holes 102a-102c.

Once the target end point(s) 402a-402c and target axes 401a-401c have been created, software associated with CAS system 200 may establish a plurality of virtual haptic geometries 400a-400c. According to one embodiment, virtual haptic geometries 400a-400c may each embody funnel-shaped haptic guide zones, such as that shown in FIG. 5. It is contemplated, however, that additional and/or different sizes and shapes of haptic geometries may be used without departing from the scope of the present disclosure.

During operation, CAS system 200 may be configured to identify target points 402a-402c (or other aspect of virtual haptic geometries 400a-400c, such as bone surface engagement points 605a-605c) and determine the position of reference point 103a of cutting tool 103 (Step 720). Specifically, CAS system 200 may identify the position of a predetermined feature of each of virtual haptic geometries 400a-400c as a basis for comparison with the position of reference point 103a. This predetermined feature may be any feature associated with virtual haptic geometries 400a-400c that can be used as a reference for determining which of virtual haptic geometries 400a-400c is closest to reference point 103a of cutting tool 103. For example, the predetermined feature may comprise target points 402a-402c, engagement points 605a-605c, or a particular point on boundary surface 404 of each of virtual haptic geometries 400a-400c.

Upon identifying the plurality of planned target points associated with surgical environment 100, the distance from reference point 103a of cutting tool 103 to each target point may he determined (Step 730). According to one embodiment, tracking system 201 of CAS system 200 may determine the position of reference point 103a of a surgical instrument (e.g., cutting tool 103) within surgical environment 100. Software associated with CAS system 200 may be configured to calculate the distance between the position of reference point 103a and each target end point 402a-402c. Alternatively or additionally, software associated with CAS system 200 may be configured to determine the distance between reference point 103a and other aspects of surgical environment 100, such as target engagement points 605a-605c. Accordingly, "target point," as the term is used herein, refers to any feature or point associated with surgical environment 100 that may be targeted for engagement by cutting tool 103, such as, for example, target engagement points 605a-605c and target end points 402a-402c.

Once the distance from reference point 103a to each target point has been determined, the target point that is closest to reference point 103a may be identified (Step 740). Specifically, software associated with CAS system 200 may compare the distances between reference point 103a and each of the target points to identify the target point that is closest to reference point 103a. Based on the identified target point, CAS system 200 may activate the respective haptic geometry (e.g., virtual haptic geometry 400a of FIG. 6) associated with the identified target point (Step 750). The remaining virtual haptic geometries (e.g., virtual haptic geometries 400b, 400c of FIG. 6) may remain inactive while virtual haptic geometry 400a is active. According to the exemplary embodiment, only haptic forces associated with "active" virtual haptic geometries can operate to constrain the position and orientation of cutting tool 103.

It is contemplated that, although certain embodiments are described as using distance between reference point 103a and target points 402a-402c as the basis for determining which of virtual haptic geometries 400a-400c is activated, other features may be used for selectively activating virtual haptic geometries 400a-400c. For example, CAS system 200 may be configured to determine the position of reference point 103a of cutting tool 103 relative to an engagement area (defined by a height, h, above the surface of bone 101 and a distance, d, from the target axis 401) associated with each post hole. If the position of reference point 103a enters the engagement area corresponding to a particular post hole, the virtual haptic geometry 400a-400c associated with the engagement area may be activated.

FIG. 8 provides a flowchart 800 illustrating an exemplary embodiment for sequentially activating virtual haptic geometries associated with surgical environment 100. As illustrated in FIG. 8, the method may include monitoring a position of reference point 103a of cutting tool 103 (Step 810). According to the exemplary embodiments described above, tracking system 201 of CAS system 200 may be configured to monitor the position of reference point 103a relative to one or more other registered components of surgical environment within the virtual coordinate space.

While tracking the position of tool reference point 103a, CAS system 200 may be configured to determine whether tool reference point 103a is within a threshold distance of a target point associated with one of the available or "open" virtual haptic geometries 400a-400c (Step 820). According to one embodiment, virtual haptic geometries 400a-400c may be designated as "open" if the surgical plan has not yet been completed for the respective virtual haptic geometry. Turning to FIG. 6, for example, each of virtual haptic geometries 400a-400c may be designated as "open" until the reference point 103a of cutting tool 100 has resected all of the bone within the volume defined by the respective virtual haptic geometry.

Once the resected bone has been removed and the post hole has been completed, CAS system 200 may "close" the virtual haptic geometry and deactivate the haptic boundary associated therewith. CAS system 200 is configured to estimate the completion of the bone resection process by tracking the location of reference position 103a of cutting tool 103 relative to the bone and the respective virtual haptic geometry 400a-400c associated therewith. For example, CAS system 200 may determine that the bone resection operation for a first post hole is complete when reference point 103a of cutting tool 103 has successfully reached target end point 402a, which corresponds to the bottom of post hole 102a.

If CAS system 200 determines that tool reference point 103a is not within a threshold distance of a target point associated with an "open" virtual haptic geometry (Step 820: No), the process may revert back to step 810, whereby CAS system 200 continues to monitor the position of tool reference point 103a. If, on the other hand, CAS system 200 determines that reference point 103a is within a threshold distance of an "open" target point (Step 820: Yes), CAS system 200 may activate the respective virtual haptic geometry associated with the corresponding target point (Step 830). CAS system 200 may deactivate the remaining virtual haptic geometries (and/or haptic forces associated therewith), so that haptic forces associated with the remaining geometries do not interfere with haptic forces corresponding to the active virtual haptic geometry.

Once the virtual haptic geometry is activated and tool reference point 103a is located therewithin, CAS system 200 may be configured to determine whether tool reference position 103a is trying to "break" out of the haptic volume defined by the virtual haptic geometry (Step 835). According to one embodiment, this involves tracking the position of tool reference point 103a within the volume defined by virtual haptic geometry 400. The tracked position of reference point 103a may be compared with the position of boundary surface 404. Tracking system 201 of CAS system 200 may be configured to determine when the position of reference point 103a interferes, intersects, or otherwise overlaps with boundary surface 404. As the position of reference point 103a interferes with the position of boundary surface 404, CAS system 200 may be configured to detect that reference point 103a is trying to "break" through the haptic boundary defined by virtual haptic geometry 400.

If tracking system 201 associated with CAS system 200 determines that reference point 103a is trying to "break" through boundary surface 404 associated with virtual haptic geometry 400 (Step 835: Yes), force system of CAS system 200 may be configured to apply corresponding haptic forces to constrain the tool reference point within the haptic volume (Step 840). According to one embodiment, CAS system 200 is configured as an impedance-type haptic system, whereby haptic forces are designed to simulate a mechanical impedance based on the position of reference point 103a relative to boundary surface 404 of virtual haptic geometry 400. It is contemplated, however, that, that processes and methods consistent with the disclosed embodiments are also compatible with admittance-type haptic force control systems. CAS system 200 may continue monitoring the position of the tool reference point 103a (Step 855) and revert back to step 835.

If, however, tool reference point 103a is not trying to break out of the volume defined by virtual haptic geometry (Step 835: No), CAS system is programmed to monitor the progress of reference point 103a of cutting tool 103 and determine whether the reference point 103a has reached the target end point (Step 850). If reference point 103a has not reached target end point (Step 850: No), the process may continue to monitor the position of tool reference point 103a (Step 855) and revert back to step 835.

After reference point 103a has reached target point (Step 850: Yes), CAS system may determine when the reference point has been safely extracted from the bone engagement surface (Step 860: Yes) before deactivating and closing the haptic guide zone (Step 880). Specifically, CAS system 200 may determine when the position of reference point 103a of cutting tool 103 has been moved outside of an engagement threshold (not shown). This engagement threshold may embody a user-defined (or predetermined) virtual boundary that is used as a trigger for deactivating and closing a virtual haptic geometry upon completion of bone resection process. To ensure that virtual haptic geometry remains active after the post hole is complete in order to help guide cutting tool 103 while it is being extracted from the hole, the engagement threshold may be established as a distance from the surface of the bone. According to one embodiment, this distance may be similar to that used to define intermediate tool stop plane (shown as 420 of FIG. 5).

If reference point 103a has not been extracted outside of the predetermined engagement area (or distance) (Step 860: No), CAS system 200 may continue monitoring the position of tool reference point 103a (Step 870) and revert back to step 860. If, however, reference point 103a been extracted outside of the predetermined engagement threshold (Step 860: Yes), CAS system 200 may deactivate the virtual haptic geometry (and haptic forces associated therewith) and "close" the post hole from further access by cutting tool 103 (Step 880). The process may then revert back to step 810, to continue selective activation of the remaining (i.e., "open") virtual haptic boundaries.

As explained above, there are many alternatives for determining which of virtual haptic geometries should be activated based on the position of reference point 103a. For example, as an alternative or in addition to determining whether tool reference point 103a is within a threshold distance of an "open" target point associated with a virtual haptic geometry, CAS system 200 may be configured to determine whether tool reference point 103a is within a threshold engagement area (or volume) associated with a virtual haptic geometry.

Alternatively, a combination of criteria may be used to determine which of virtual haptic geometries 400a-400c is to be activated. For example, CAS system 200 may be configured to require that reference point 103a (1) be located within the volume defined by a virtual haptic geometry and (2) be within the threshold engagement area associated with the post hole. FIG. 6 illustrates virtual haptic geometry 400a, which has been activated using this multiple-criteria approach for activating virtual haptic geometries. By using multiple criteria for activating virtual haptic geometries, CAS system 200 may be configured to avoid "accidental" activation of haptic boundaries, which is more likely to occur where only a single criterion is used.

It is also contemplated that CAS system 200 may include a solution for manually overriding the activation of virtual haptic geometries. According to one embodiment, this manual override feature may allow the user to selectively activate (and deactivate) the virtual haptic geometries based on the specific needs/preferences of the surgeon. Thus, an activated virtual haptic geometry 400a may be manually deactivated, allowing the surgeon to selectively activate one of the other virtual haptic geometries 400b, 400c. It should be noted that virtual haptic geometry 400a may remain "open" after the manual override, unless cutting tool 103 has completed the resection of the bone associated with virtual haptic geometry 400a. It should also be noted that the manual activate/deactivation feature may be disabled in certain situations, such as when reference point 103a is located within bone (and/or the cylindrical portion of virtual haptic geometry 400a) or when reference point 103a is located within a predetermined distance of the surface of bone 101.

Although virtual haptic geometry is illustrated and described in the exemplary embodiments as being a substantially funnel-shaped boundary for use in guiding a surgical drill or burr to a target point, the presently disclosed embodiments are applicable for generating virtual haptic boundaries having different shapes for use with other types of tools. For example, the presently disclosed embodiments contemplate generating a collapsible virtual haptic geometry having a substantially "Y"-shaped cross section having a substantially "V"-shaped upper section that converges to a substantially planar lower section for guiding a planar or sagittal saw toward a desired orientation for executing a planar cut on a bone. Consequently, it is contemplated that the methods described herein may be employed in virtually any environment where it may be advantageous to guide a surgical tool to a predetermined orientation for approaching a target tool operation site.

The presently disclosed systems and methods provide a solution that enables a computer-assisted surgical system to sequentially and/or selectively activate virtual haptic guide zones, thereby ensuring that overlapping haptic guide zones do not interfere with one another during operation of cutting tool 103. More specifically, certain systems and methods described herein implement a process that determines the position of a reference point 103a of a surgical instrument and, based on this position, automatically activates the nearest available virtual haptic guide zone. Once one of the haptic guide zones is activated, haptic forces associated with the activated zone guide the tool until the assigned task has been completed, the target end point has been reached, or the haptic guide zone has been deactivated by the surgeon. This process may be repeated until each of the tasks associated with the haptic guide zones have been completed and the corresponding virtual haptic geometries have been closed.

CAS systems 200 configured in accordance with the presently disclosed embodiments may have several advantages. For example, by providing a solution for selectively and/or sequentially activating haptic guide zones, problems associated with interference between adjacent overlapping haptic boundaries may be significantly reduced. Furthermore, because the presently disclosed embodiments provide a solution for automatically activating (and deactivating) haptic guide zones based on the position of cutting tool 103, inefficiencies associated with avoiding regions of overlapping haptic boundaries may be minimized or eliminated.

The foregoing descriptions have been presented for purposes of illustration and description. They are not exhaustive and do not limit the disclosed embodiments to the precise form disclosed. Modifications and variations are possible in light of the above teachings or may be acquired from practicing the disclosed embodiments. For example, the described implementation includes software, but the disclosed embodiments may be implemented as a combination of hardware and software or in firmware. Examples of hardware include computing or processing systems, including personal computers, servers, laptops, mainframes, micro-processors, and the like. Additionally, although disclosed aspects are described as being stored in a memory one skilled in the art will appreciate that these aspects can also be stored on other types of computer-readable storage devices, such as secondary storage devices, like hard disks, floppy disks, a CD-ROM, USB media, DVD, or other forms of RAM or ROM.

It will be apparent to those skilled in the art that various modifications and variations can be made to the disclosed systems and associated methods for selectively activating haptic guide zones without departing from the scope of the present disclosure. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A method for operating a surgical robot, comprising:
providing a plurality of virtual haptic geometries associated with different steps of a surgical procedure;
evaluating a plurality of criteria associated with a first virtual haptic geometry of the plurality of virtual haptic geometries;
in response to satisfaction of the plurality of criteria, activating the first virtual haptic geometry of the plurality of virtual haptic geometries without activating a second virtual haptic geometry of the plurality of virtual haptic geometries;
controlling the surgical robot to constrain movement of an end effector of the surgical robot to the first virtual haptic geometry in response to activating the first virtual haptic geometry; and
preventing reactivation of the first virtual haptic geometry of the plurality of virtual haptic geometries in response to completion of a first step of the surgical procedure associated with the first virtual haptic geometry.

2. The method of claim 1, wherein evaluating the plurality of criteria comprises determining a position of the end effector relative to the first virtual haptic geometry.

3. The method of claim 2, wherein evaluating the plurality of criteria comprises determining whether the position of the end effector is both within the first virtual haptic geometry and within a threshold engagement volume associated with the first virtual haptic geometry.

4. The method of claim 2, further comprising evaluating a first criterion of the plurality of criteria by determining whether the position of the end effector is within a threshold distance of a target axis of the first virtual haptic geometry.

5. The method of claim 1, further comprising preventing the activation of the first virtual haptic geometry when one or more of the plurality of criteria is unsatisfied.

6. The method of claim 1, wherein providing the plurality of virtual haptic geometries comprises determining a plurality of target points in a surgical environment and associating the plurality of virtual haptic geometries with the plurality of target points.

7. The method of claim 1, wherein providing the plurality of virtual haptic geometries comprises configuring the plurality of virtual haptic geometries to have different shapes.

8. The method of claim 1, further comprising reducing a volume of the first virtual haptic geometry in response to a surgeon movement.

9. The method of claim 8, wherein reducing the volume of the first virtual haptic geometry comprises collapsing a funnel shape of the first virtual haptic geometry such that the end effector is rotatable only towards alignment with a target axis of the first virtual haptic geometry.

10. The method of claim 1, wherein the first virtual haptic geometry defines a virtual pathway to guide the end effector into a planned alignment relative to an anatomical structure to be modified in the surgical procedure.

11. The method of claim 1, wherein controlling the surgical robot to constrain movement of the end effector of the surgical robot to the first virtual haptic geometry comprises allowing the end effector to pass through an opening of the first virtual haptic geometry to disengage from the first virtual haptic geometry.

12. The method of claim 1, wherein evaluating the plurality of criteria associated with the first virtual haptic geometry of the plurality of virtual haptic geometries is performed responsive to determining that a first target point associated with the first virtual haptic geometry is closer to the end effector than a second target point associated with the second virtual haptic geometry.

13. A system, comprising:
a surgical robot comprising an end effector;
a processor, and
one or more non-transitory computer-readable media storing program instructions that, when executed by the processor, cause the processor to perform operations comprising:
providing a plurality of virtual haptic geometries associated with different steps of a surgical procedure;
evaluating a plurality of criteria associated with a first virtual haptic geometry of the plurality of virtual haptic geometries;
in response to satisfaction of the plurality of criteria, activating the first virtual haptic geometry of the plurality of virtual haptic geometries without activating a second virtual haptic geometry of the plurality of virtual haptic geometries;
controlling the surgical robot to constrain movement of the end effector of the surgical robot to the first virtual haptic geometry in response to activating the first virtual haptic geometry; and
preventing reactivation of the first virtual haptic geometry of the plurality of virtual haptic geometries in response to completion of a first step of the surgical procedure associated with the first virtual haptic geometry.

14. The system of claim 13, wherein evaluating the plurality of criteria comprises determining a position of the end effector relative to the first virtual haptic geometry.

15. The system of claim 14, wherein evaluating the plurality of criteria comprises determining whether the position of the end effector is both within the first virtual haptic geometry and within a threshold engagement volume associated with the first virtual haptic geometry.

16. The system of claim 13, wherein the operations further comprise reducing a volume of the first virtual haptic geometry in response to a surgeon movement.

17. The system of claim 16, wherein reducing the volume of the first virtual haptic geometry comprises collapsing a funnel shape of the first virtual haptic geometry such that the end effector is rotatable only towards alignment with a target axis of the first virtual haptic geometry.

18. The system of claim 13, wherein evaluating the plurality of criteria associated with the first virtual haptic geometry of the plurality of virtual haptic geometries is performed responsive to determining that a first target point associated with the first virtual haptic geometry is closer to the end effector than a second target point associated with the second virtual haptic geometry.

19. The system of claim 13, wherein controlling the surgical robot to constrain movement of the end effector of the surgical robot to the first virtual haptic geometry comprises allowing the end effector to pass through an opening of the first virtual haptic geometry to disengage from the first virtual haptic geometry.

* * * * *